United States Patent
Cohen et al.

[11] Patent Number: 5,695,487
[45] Date of Patent: Dec. 9, 1997

[54] Z-DIRECTON LIQUID TRANSPORT MEDIUM

[75] Inventors: Bernard Cohen, Berkeley Lake; Lee Kirby Jameson, Roswell; Roger Bradshaw Quincy, III, Alpharetta, all of Ga.

[73] Assignee: Kimberly-Clark Worldwide, Inc., Neenah, Wis.

[21] Appl. No.: 733,033

[22] Filed: Oct. 16, 1996

Related U.S. Application Data

[63] Continuation of Ser. No. 303,787, Sep. 9, 1994, abandoned.

[51] Int. Cl.$^6$ ........................................... A61F 13/15
[52] U.S. Cl. ........................................ 604/384; 604/378
[58] Field of Search ........................... 604/378, 384, 604/385.1

[56] References Cited

U.S. PATENT DOCUMENTS

| | | |
|---|---|---|
| 810,133 | 1/1906 | Green . |
| 810,135 | 1/1906 | Green . |
| 1,669,295 | 5/1928 | Hallenberg . |
| 2,444,528 | 7/1948 | Popper et al. . |
| 2,508,214 | 5/1950 | Biederman . |
| 2,960,089 | 11/1960 | Harwood et al. . |
| 3,085,309 | 4/1963 | Olson . |
| 3,095,878 | 7/1963 | Bassett . |
| 3,101,520 | 8/1963 | George et al. . |
| 3,236,238 | 2/1966 | Morse . |
| 3,315,676 | 4/1967 | Cooper . |
| 3,431,337 | 3/1969 | Heimberger . |
| 3,460,536 | 8/1969 | Champaigne, Jr. ............ 128/290 |
| 3,525,337 | 8/1970 | Simons et al. ................. 128/298 |
| 3,561,446 | 2/1971 | Joned ............................ 128/287 |
| 3,563,242 | 2/1971 | Hedstrom et al. ............. 128/287 |
| 3,610,244 | 10/1971 | Jones ............................. 128/287 |
| 3,653,382 | 4/1972 | Easley et al. ................. 128/284 |
| 3,973,068 | 8/1976 | Weber ............................ 428/198 |
| 4,070,218 | 1/1978 | Weber ............................ 156/167 |
| 4,119,450 | 10/1978 | Bianco .......................... 156/199 |
| 4,389,211 | 6/1983 | Lenaghan ...................... 604/383 |
| 4,532,173 | 7/1985 | Suzuki et al. ................. 428/218 |
| 4,559,050 | 12/1985 | Iskra .............................. 604/368 |
| 4,568,341 | 2/1986 | Mitchell et al. .............. 604/368 |
| 4,576,853 | 3/1986 | Vaughn et al. ................ 428/181 |
| 4,578,070 | 3/1986 | Holtman . |
| 4,605,402 | 8/1986 | Iskra .............................. 604/368 |
| 4,627,848 | 12/1986 | Lassen et al. . |
| 4,636,209 | 1/1987 | Lassen ........................... 604/378 |
| 4,655,760 | 4/1987 | Morman et al. ............... 604/385 |
| 4,681,577 | 7/1987 | Stern et al. . |
| 4,699,808 | 10/1987 | Menard et al. ................ 427/180 |

(List continued on next page.)

FOREIGN PATENT DOCUMENTS

| | | |
|---|---|---|
| 0 140 471 | 5/1985 | European Pat. Off. . |
| 0 159 671 | 10/1985 | European Pat. Off. . |
| 93-011727 | 6/1993 | WIPO . |
| 94 05244 | 3/1994 | WIPO . |

*Primary Examiner*—Michael J. Milano
*Attorney, Agent, or Firm*—William E. Maycock

[57] ABSTRACT

A fibrous web having a length, a width and a thickness, with at least about 50 percent of the fibers aligned in a direction generally perpendicular to the length and width of the web. The web defines a plurality of spaced-apart gaps, each having a top and a bottom, and each of the gaps extends from one surface of the web at least about 50 percent through the thickness of the web. The density of a portion of the web defining the bottom of the gap is greater than the density of a portion of the web defining the top of the gap. The portion of the web which defines the top of the gap may be composed substantially of terminal ends of the fibers. In addition, the portion of the web which defines the bottom of the gap may be composed substantially of continuous fibers. The fibrous web may be a meltblown nonwoven web or a neck-stretched, meltblown nonwoven web. The fibrous web may be employed as a component of such absorbent products as diapers; incontinent care products; and feminine care products, such as sanitary napkins and tampons; filter elements; and the like. The web provides improved distribution of liquid in the direction of fiber alignment.

13 Claims, 3 Drawing Sheets

U.S. PATENT DOCUMENTS

| | | | |
|---|---|---|---|
| 4,723,954 | 2/1988 | Pieniak . | |
| 4,793,280 | 12/1988 | Menard et al. | 118/44 |
| 4,923,914 | 5/1990 | Nohr et al. | 524/99 |
| 4,965,122 | 10/1990 | Morman | 428/225 |
| 5,102,738 | 4/1992 | Bell et al. | 428/411.1 |
| 5,112,690 | 5/1992 | Cohen et al. | 428/411.1 |
| 5,244,723 | 9/1993 | Anderson et al. | 428/283 |

Z-DIRECTON LIQUID TRANSPORT MEDIUM

This application is a continuation of application Ser. No. 08/303,787 entitled "Z-DIRECTION LIQUID TRANSPORT MEDIUM" and filed in the U.S. Patent and Trademark Office on Sep. 9, 1994 now abandoned. The entirety of this application is hereby incorporated by reference.

BACKGROUND OF THE INVENTION

The present invention relates to a liquid transport medium, and to a liquid transport medium which is a component of an absorbent product.

Absorbent products currently find wide-spread use, many of which are intended for limited or even single use. Typical of such products are diapers; incontinent care products; feminine care products, such as sanitary napkins and tampons; filter elements; wipes; surgical gowns and drapes; protective pads; wound dressings, such as bandages; and the like. A number of these products have an absorbent core which is covered by a layer of fabric, often a nonwoven web, commonly referred to as an outer cover. It usually is the outer cover which is touched or handled or, for body-contacting products, is adjacent to the skin during use.

Many absorbent products are concerned with, at least to some degree, the distribution of liquid to which the product is exposed. Liquid distribution is a concern because it has an effect, to a greater or lesser extent, on such aesthetic qualities as appearance, particularly during and after use.

Liquid distribution, sometimes referred to as wicking, generally involves the movement of liquid away from the locus of liquid insult to the remainder of the absorbent product. Distribution, in effect, makes more of the absorbent product available for absorption of liquid. Although distribution can be in any direction, distribution in the Z-direction (i.e., through the thickness of the product) is particularly important when comfort and aesthetic considerations are involved, such as feeling dry to the skin, either as worn or when handled, and after-use appearance. The latter is particularly important for products which are used to absorb colored materials such as blood or menses.

Improving Z-direction wicking has in the past involved a significant research and development effort. Although much progress has been made, opportunities still remain for further improvements in Z-direction liquid distribution.

SUMMARY OF THE INVENTION

The present invention addresses some of the difficulties and problems discussed above by providing a fibrous web having a length, a width and a thickness, with at least about 50 percent of the fibers aligned in a direction generally perpendicular to the length and width of the web. The web defines a plurality of spaced-apart gaps, each having a top and a bottom, and each of the gaps extends from one surface of the web at least about 50 percent through the thickness of the web. The density of a portion of the web defining the bottom of the gap is greater than the density of a portion of the web defining the top of the gap. The fibers of which the fibrous web is composed are wettable by a liquid to which the fibrous web may be exposed.

The portion of the web which defines the top of the gap may be composed substantially of terminal ends of the fibers. In addition, the portion of the web which defines the bottom of the gap may be composed substantially of continuous fibers.

The fibrous web may be a meltblown nonwoven web or a neck-stretched, meltblown nonwoven web. Other materials in which the fibers are significantly oriented in the required direction also may be employed.

The fibers of which the fibrous web are composed may be hydrophilic. Alternatively, the fibers may have hydrophilic surfaces. In the latter case, the fibers desirably have been treated with a surfactant and exposed to a corona field.

One embodiment of the fibrous web is a Z-direction liquid transport medium defining a plurality of generally V-shaped troughs, each of which has a bottom portion and a top portion and is composed of a fibrous web. The fibers of the fibrous web are significantly oriented in a direction generally extending from the top portion of each trough to the bottom portion thereof. In addition, the fibers are wettable by a liquid to which the medium may be exposed. Moreover, the density of the web at the bottom of each trough is greater than the density of the web in the remainder of the trough. Finally, the fibers at the top portion of each trough are substantially discontinuous from the fibers at the top portions of adjacent troughs.

The Z-direction liquid transport medium may be prepared by the method which involves providing a fibrous web in which the fibers are significantly oriented in one direction and wettable by a liquid to which the medium may be exposed. The fibrous web is formed into a plurality of troughs, each of which has a bottom portion and a top portion, in a manner such that the fibers are significantly oriented in a direction generally extending from the top portion of each trough to the bottom portion thereof, the density of the web at the bottom of each trough is greater than the density of the web in the remainder of the trough, and the fibers at the top portion of each trough are substantially discontinuous from the fibers at the top portions of adjacent troughs.

The fibrous web of the present invention may be employed as a component of such absorbent products as diapers; incontinent care products; and feminine care products, such as sanitary napkins and tampons; as well as filter elements; and the like. For example, the fibrous web may be employed between the absorbent core and the outer cover of an absorbent product, such as a sanitary napkin, to aid in the distribution of fluid to the absorbent core.

DETAILED DESCRIPTION OF THE INVENTION

Figure 1:
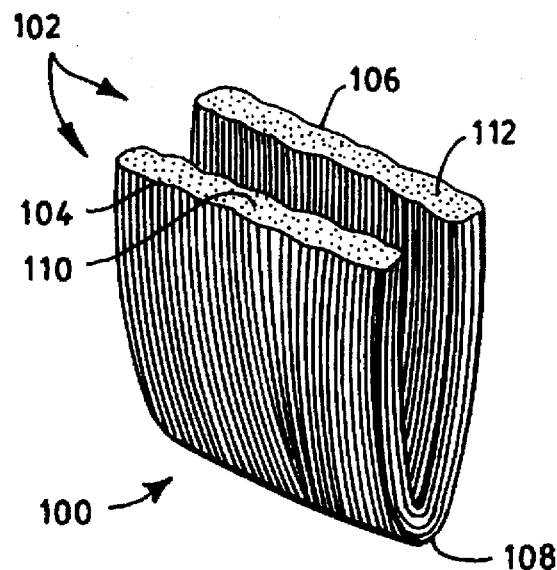
FIG. 1 is a diagrammatic perspective view of a portion of one embodiment of a fibrous web of the present invention.

As used herein, the term "machine direction" means a direction which is essentially parallel with the motion of a nonwoven web through the web-forming apparatus as the web is formed; i.e., a direction which is parallel with the direction of the forming wire upon which the nonwoven web is formed. The term "cross-direction" is used herein to mean a direction which is the cross machine direction, i.e., a direction which is perpendicular to the machine direction.

As used herein, the term "Z-direction" means a direction which is through the thickness of the product, i.e., the direction of fiber alignment. Thus, the Z-direction is normal to the length and width, or machine direction and cross-direction, of an absorbent product (or component thereof, such as a nonwoven web).

The term "trough" is intended herein to have its usual meaning. The term, however, is not intended to imply dimensional relationships, such as length or width to height, or to refer to the space defined by a trough.

The term "liquid" is used herein to mean any liquid. As a practical matter, the liquid most often will be water. When the fibrous web of the present invention is employed in an absorbent product, the liquid typically will be bodily excrement, such as urine, blood, menses, serum, and the like.

The fibrous web has a length, a width and a thickness, with at least about 50 percent of the fibers aligned in a direction generally perpendicular to the length and width of the web. By way of illustration, the fibrous web may be a web composed of fibers, in which the fibers are significantly oriented in one direction. In general, any fibrous web can be employed in which the foregoing fiber orientation requirement is met.

For example, the material may be a nonwoven web prepared by a meltextrusion process which significantly orients fibers in one direction. Meltblowing is an example of such a process, in which case the direction of fiber orientation is in the machine direction. While meltblown nonwoven webs are known to result in a significant orientation of the fibers, it is not possible to measure with certainty the degree of such orientation, primarily because of the random nature of fiber deposition on the forming wire. It has been estimated, however, that the ratio of the number of fibers oriented substantially in the machine direction to the number of fibers oriented substantially in the cross direction is greater than 1:1.

As another example, the material may be a neck-stretched, meltblown nonwoven web. Neck-stretching is a known procedure which increases the orientation of fibers in the direction of stretch; see, e.g., U.S. Pat. No. 4,695,122 to Morman, which patent is incorporated herein by reference.

As a further example, the material may be a web formed by hydraulic spinning. Such a web is comprised of filaments which are highly oriented in the machine direction; see U.S. Pat. No. 5,244,723 to Anderson, which patent is incorporated herein by reference. Because of the high degree of orientation of the filaments, it may be desirable to employ a hydraulically spun web in conjunction with one or more support webs. For example, a hydraulically spun web may be bonded to another nonwoven web, such as a meltblown, coformed, spunbonded, or carded and bonded web. Alternatively, a hydraulically spun web may be sandwiched between two other nonwoven webs, either or both of which may be a meltblown web or a neck-stretched, meltblown web.

In general, the fibers of the web may be of any composition which may be formed into fibers. Thus, the fibers may be natural fibers or fibers prepared from synthetic materials. Natural fibers include, for example, cellulose and cellulose derivatives, wool, cotton, and the like. Synthetic materials include thermosetting and thermoplastic polymers. The term "polymer" is meant to include blends of two or more polymers and alternating, random, block, and graft copolymers prepared from two or more different starting materials or monomers.

Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly (chlorotrifluoroethylene), ethylene-chlorotrifluoroethylene copolymers, poly(vinylidene fluoride), poly(vinyl fluoride), and the like; polyamides, such as poly(6-aminocaproic acid) or poly(-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenyleneoxy-1,4-phenylenesulfonyl-4,4'-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; copolymers of the foregoing, such as acrylonitrile-butadiene-styrene (ABS) copolymers, and the like; and the like.

The fibers may be naturally hydrophilic, i.e., hydrophilic without the incorporation of a melt additive or a topical treatment to render the fibers hydrophilic. Alternatively, the fibers may be prepared from a hydrophobic polymer, in conjunction with the use of either a melt additive or a topical treatment to render the fibers hydrophilic. A melt additive may be employed as described in, for example, U.S. Pat. No. 3,973,068 to Weber; U.S. Pat. No. 4,070,218 to Weber; and U.S. Pat. No. 4,923,914 to Nohr and MacDonald, which patents are incorporated herein by reference. When a hydrophobic polymer is employed for the preparation of the fibers, the polymer may be, by way of illustration, a polyolefin as defined above. Particularly desirable polyolefins are polyethylene and polypropylene. However, the use of a hydrophilic polymer to prepare the fibers does not preclude the treatment of the fibers with, for example, a surfactant.

In addition to being significantly oriented in one direction, the fibers of the web may be treated with a surfactant and exposed to a corona field. In general, the surfactant can be any surfactant known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow trimethylammonium chloride. Examples of nonionic surfactants, include, again by way of illustration only, alkyl polyethoxylates; polyethoxylated alkylphenols; fatty acid ethanol amides; and complex polymers of ethylene oxide, propylene oxide, and alcohols. Desirably, the surfactant will be a nonionic surfactant.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other.

In general, an amount of surfactant typically will be employed which is sufficient to achieve the desired increase in Z-direction wicking. Such amount can vary widely. As a practical matter, the amount of surfactant present on the fibers of the material will be in a range of from about 0.1 to about 5 weight percent, based on the weight of the fibers. Desirably, the amount of surfactant present on the fibers will be in a range of from about 0.5 to about 3 weight percent.

Finally, the fibers of the material desirably may be exposed to a corona field. As used herein, the term "corona field" means a corona field of ionized gas. Exposing the fibers to a corona field typically increases the effectiveness of the surfactant in enhancing distribution of a liquid in the Z-direction, i.e., in the direction of fiber orientation. Carrying out the corona field exposure after treating the fibers with surfactant is especially effective.

In general, the generation of a corona field and exposure of the fibers are accomplished in accordance with procedures which are well known to those having ordinary skill in the art. The energy density to which the fibers are exposed can range from about 1 to about 500 watt-minute per square foot (w-min/ft$^2$), which is approximately equivalent to a range of from about 0.6 to about 323 kilojoules per square meter (kJ/m$^2$). Desirably, the energy density will be in a range of from about 15 to about 350 w-min/ft$^2$ (from about 10 to about 226 kJ/m$^2$).

The combination of topically applied surfactant and subsequent corona field exposure are described in U.S. Pat. No. 5,102,738 to Bell et al. and U.S. Pat. No. 5,112,690 to Cohen et al., which patents are incorporated herein by reference.

One embodiment of the fibrous web of the present invention is a Z-direction liquid transport medium defining a plurality of generally V-shaped troughs, each of which has a bottom portion and a top portion and is comprised of a fibrous web, in which:

the fibers are significantly oriented in a direction generally extending from the top portion of each trough to the bottom portion thereof;

the density of the web at the bottom of each trough is greater than the density of the of web in the remainder of the trough; and the fibers at the top portion of each trough are substantially discontinuous from the fibers at the top portions of adjacent troughs.

One of the V-shaped troughs of this embodiment is illustrated diagrammatically in a perspective view in FIG. 1. FIG. 1 shows a trough 100 having a bifurcated top portion 102, consisting of a first side portion 104 and a second side portion 106, and a bottom portion 108. The first side portion 104 has a face 110 and the second side portion 106 has a face 112. Each of the faces 110 and 112 is composed substantially of terminal ends of the fibers of which the trough 100 is composed.

It will be readily apparent to those having ordinary skill in the art that the method employed to prepare the fibrous web of the present invention will depend in large measure on the particular embodiment desired. For example, the Z-direction liquid transport medium described above can be prepared by a number of methods. For example, each generally V-shaped trough can be prepared individually and a number of the troughs then can be assembled as desired. An individual trough may be prepared by laying a section of a fibrous web over a plate having a groove or notch of the shape desired for the trough. The section of fibrous web then may be pushed into the groove or notch with a thin rigid sheet. If necessary, the side portions may be trimmed to any desired height. Alternatively, the section of fibrous web may be sized such that, when pushed into the groove or notch, the side portions are the desired height. As another example, a fibrous sheet may be folded back and forth, or corrugated, and then abraded on one side to give a plurality of troughs, as shown in the examples.

When the embodiment desired comprises the Z-direction liquid transport medium as described above, it may be desirable to utilize one or more support members for the plurality of troughs. For example, one or more support strips may be bonded to the bottom portions of the troughs. Alternatively, a sheet material, such as a nonwoven web, may be bonded to the bottom portions of the troughs, either at only selected points along each trough or along the entire length thereof. The plurality of troughs also may be sandwiched between two sheets in order to hold the troughs in place, with or without bonding of the troughs to either or both sheets. In addition to or in place of support members, interfiber bonding may be employed by, for example, the use of binders or adhesives, bicomponent fibers having a low melting component, or the like.

The present invention is further described by the example which follows. Such example, however, is not to be construed as limiting in any way either the spirit or the scope of the present invention.

EXAMPLE

Three Z-direction liquid transport media were prepared, with each defining a plurality of generally V-shaped troughs as described hereinbefore. Each medium was prepared from a sample of neck-stretched, meltblown nonwoven web prepared from polypropylene and having a basis weight of about 51 grams per square meter (g/m²). Each sample of nonwoven web measured approximately 10 cm by 40 cm. The first medium (Medium A) was prepared from nonwoven web which had not been treated in any manner and served as a control. The second medium (Medium B) was prepared from a nonwoven web which had been topically treated with a polyethoxylated alkylphenol nonionic surfactant, Triton® X-102 (Union Carbide Corporation, Danbury, Conn. at a level of about 0.6 weight percent, based on the weight of the nonwoven web. The nonwoven web was prepared by immersing the nonwoven web in 500 ml of an approximately 0.12 weight percent solution of the surfactant in water, removing the sample from the solution, passing the sample through an Atlas Laboratory Wringer with a 30-lb (13.6-kg) nip setting (Atlas Electric Devices Company, Chicago, Ill.), and allowing the sample to air dry in a fume hood. The third medium (Medium C) was prepared from a nonwoven web which first had been treated with surfactant as described for Medium B and then exposed to a corona field. Such exposure was accomplished in air at an energy density level of 219 kilojoules per square meter (kjoules/m²). Both sides of the sample were exposed to the corona field.

Corona exposure was carried out with a Corotec Laboratory Corona Treating Station with a CXC-5 Power Supply (Corotec Corporation, Collinsville, Conn.). The Treating Station utilized a pair of rotating metal rolls as electrodes, with the axes of the rolls lying in a vertical plane. Both rolls had a circumference of 12 inches (about 30.5 cm) and a diameter of about 3.8 inches (about 9.7 cm). The top roll was the anode and the bottom roll was the cathode. The bottom roll was fitted with a 2-mm-thick rubber dielectric sleeve which was in contact with the top roll, thereby providing a space of 2 mm between the electrodes. The top roll was 13 inches (about 33 cm) long and the bottom roll was about 16 inches (about 40.6 cm) long. The rolls rotated in opposite directions at a linear velocity of 12 feet per minute (about 6.1 cm per second).

Figure 2:
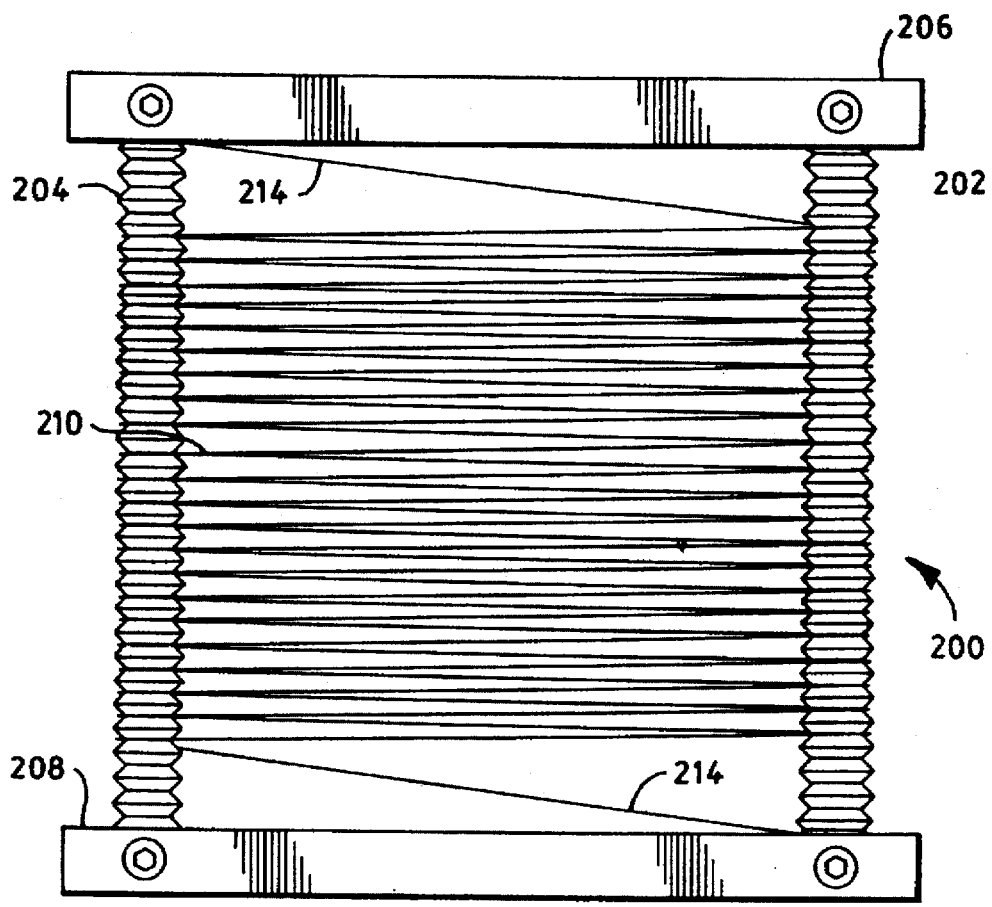
FIG. 2 is a diagrammatic plan view of a corrugating frame which may be used to prepare a fibrous web of the present invention.

Each medium was prepared with the aid of what is referred to herein for convenience as a corrugating frame. A diagrammatic plan view of the corrugating frame is shown in FIG. 2. The frame 200 consisted of a first pair of parallel side members 202 and 204 constructed from 0.5-inch (about 1.3-cm) diameter threaded stainless steel rods having about 13 threads per inch (about 5 threads per cm). The frame 200 was completed by a second pair of parallel side members 206 and 208. The second pair of parallel side members 206 and 208 also were constructed from 0.5-inch (about 1.3-cm) diameter threaded stainless steel rods having about 13 threads per inch (about 5 threads per cm), but, in order to simplify the drawing, side members 206 and 208 are shown as rectangular bars (each of side members 202 and 204 was connected to side members 206 and 208 by means of T-shaped couplers placed at each end of each of side members 206 and 208). Each side member formed 90° angles with adjacent side members. Stainless steel wire 210 having a diameter of 0.016 inch (about 0.4 mm) was spirally wound around the first pair of parallel side members 202 and 204 for a distance of 3–4 inches (7–10 cm). The two ends 212 and 214 of the wire 210 were directed to diagonal corners of the frame 200 and clamped in place (clamp not shown). Thus, the wires formed two parallel planes consisting of parallel lengths of wire.

Figure 3:
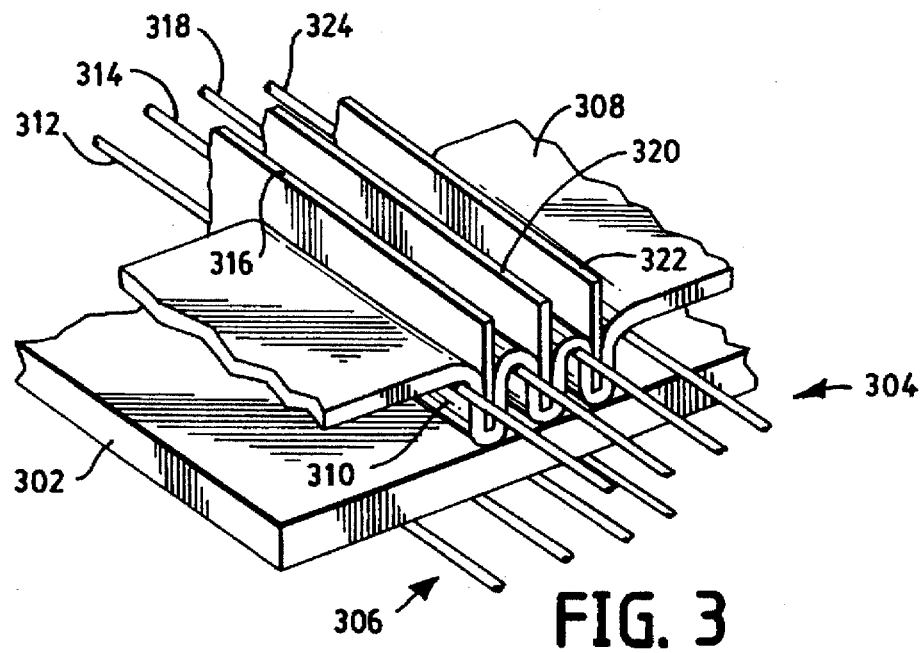
FIG. 3 is a diagrammatic perspective view of a portion of the corrugating frame of FIG. 2, illustrating the manner in which a corrugated web is formed on the frame.

The formation of a corrugated web on the corrugating frame is shown in FIG. 3 which is a diagrammatic perspective view of a portion of the corrugating frame of FIG. 2. A stop plate 302 was placed between the two planes of wires 304 and 306 and allowed to rest on the lower plane of wires 306. The thickness of the stop plate was selected so as to provide a trough thickness of about 0.19 inch (about 4.8 mm). Each sample of neck-stretched, meltblown nonwoven web 308 was placed on the upper plane of wires 304, with the longer dimension of the web normal to the wires. A portion 310 of the web 308 was pushed between adjacent wires 312 and 314 with a first thin metal plate 316 and held against the stop plate 302 by maintaining pressure on the metal plate 316. While holding the first metal plate 316 in place, the web was pushed between wire 314 and the next adjacent wire 318 with a second thin metal plate 320 until the web reached the stop plate 302. The first thin metal plate 308 was removed (shown in FIG. 3 as plate 322 for convenience) and used to push the web between wire 318 and the next adjacent wire 324. The procedure was repeated until the entire width of the sample had been corrugated. In each case, sufficient pressure was maintained by the thin metal plates to compress the web both at the bottom of each trough formed by pushing the web between adjacent wires and at each bend over a top wire. The stop plate 302 then was removed.

Figure 4:
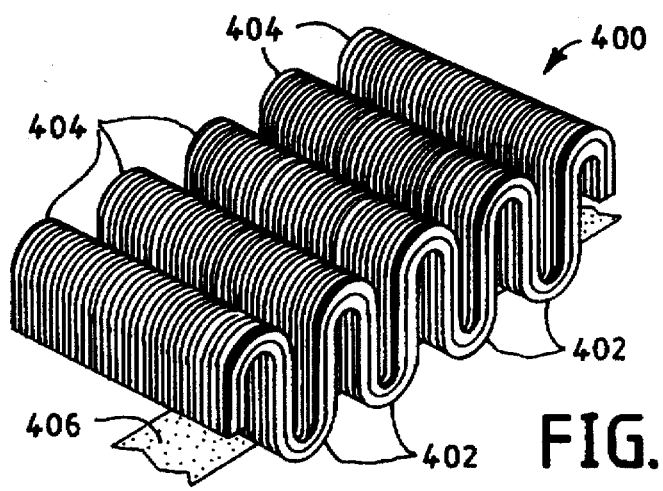
FIG. 4 is a diagrammatic perspective view of a portion of a corrugated web formed on the corrugating frame of FIG. 2.

Three strips of one-eighth inch (about 3 mm) Scotch™ Brand Magic Mending Tape were placed across the corrugated web normal to the longer dimension (i.e., normal to the corrugations). One strip was placed in the middle, and the other two strips were located about 0.5 inch (about 1.3 cm) from each end. The corrugated web then was carefully removed and turned over so that the tape strips were on the bottom. FIG. 4 is a diagrammatic perspective view of a portion of the corrugated web just described. In the figure, the portion of corrugated web 400 consists of a series of parallel corrugations have bottom portions 402 and top bend portions 404. A tape strip 406 also is shown.

Figure 5:
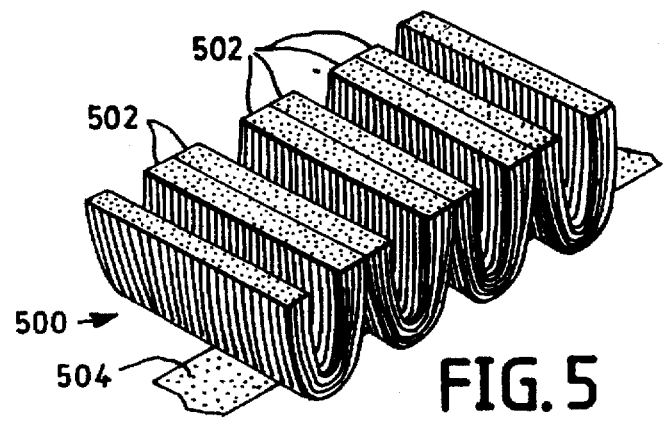
FIG. 5 is a diagrammatic perspective view of a portion of a fibrous web of the present invention obtained from the corrugated web of FIG. 4.

The upper portion of the web (i.e., upper top bend portions 404 in FIG. 4) was carefully sanded with No. 50 sandpaper to remove an amount of nonwoven web sufficient to render each trough generally independent of adjacent troughs. The resulting structure, a fibrous web of the present invention, is shown in diagrammatic perspective view in FIG. 5. The portion of fibrous web 500 consists of a series of troughs as shown in FIG. 1. The fibers at the top portion of each trough were substantially discontinuous from the fibers at the top portions 502 of adjacent troughs. A tape strip 504 also is shown.

Figure 6:
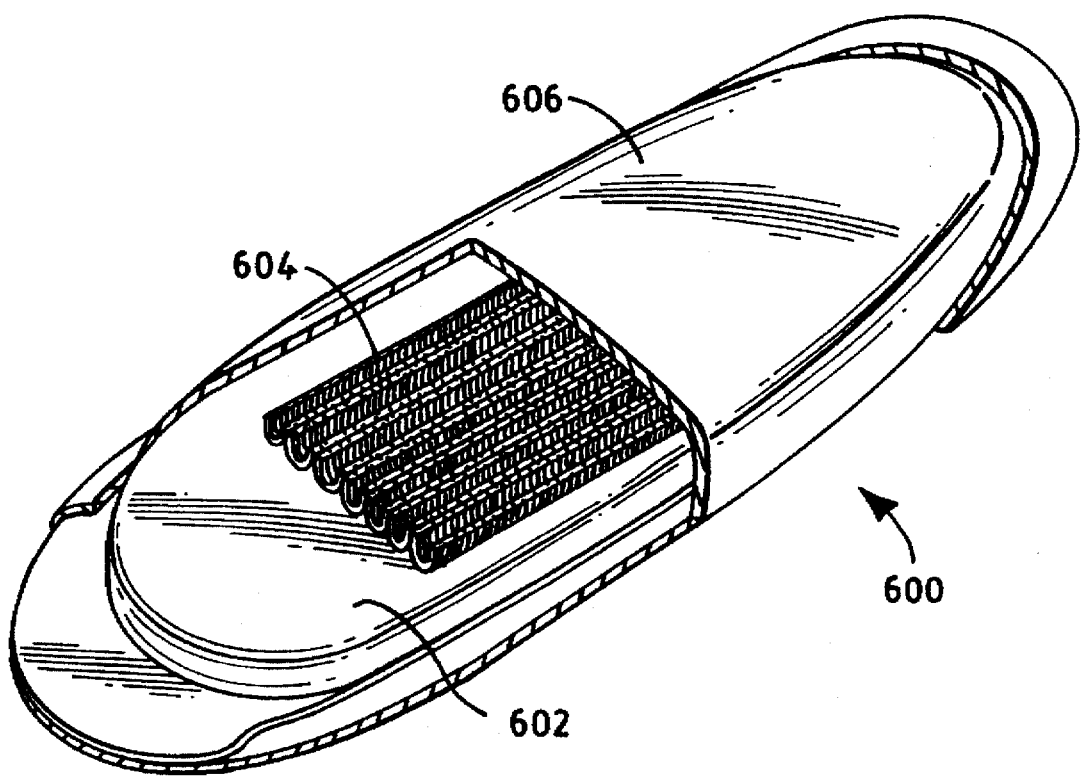
FIG. 6 is a diagrammatic perspective view of a feminine napkin having as a component thereof the fibrous web of FIG. 5.

Blood wicking characteristics for each of the three media then were tested. Testing was carried out in each case by removing the liner or cover from a Kotex® Maxi Pad (Kimberly-Clark Corporation, Neenah, Wis.), placing the medium to be tested on top of the absorbent core of the pad with the bottom portions of the troughs against the core, and laying the cover over the medium, as shown in FIG. 6. FIG. 6 is a diagrammatic perspective view of a feminine napkin having as a component thereof the fibrous web of FIG. 5. The pad 600 includes the absorbent core 602, the fibrous web 604, and the cover 606.

The reassembled Maxi Pad was placed on top of a water-filled colostomy bag which in turn was placed on a laboratory jack. An opening in the colostomy bag was connected to a manometer. The laboratory jack was raised to bring the Maxi Pad assembly against a plexiglass plate at a pressure of 0.3 pounds per square inch gauge (psig). The plate had a hole drilled through it, in which a blunt needle was located; the Maxi Pad assembly was oriented against the plate so that the needle in the plate was in the approximate center of the Pad cover. The needle was connected by a thin tube to a syringe containing bovine blood. The syringe was driven by a syringe pump set to deliver approximately 8 ml of fluid per hour. However, the actual amount of blood delivered is somewhat dependent on the resistance encountered as the blood moves from the syringe and through the thin tube to the plexiglass plate. The bovine blood was pumped onto the cover of the Maxi Pad for 30 minutes. All components of the Maxi Pad were weighed before and after each experiment, identified hereinafter as Experiments A, B, and C after the medium employed in each. The amounts of bovine blood retained by each component are summarized in Table 1. In the table, all weights are in grams (g). The "Percent" column is the amount of blood present in each component expressed as a percent of the total amount of blood present in all three components, e.g., Cover Percent=100 [Cover amt./(Cover amt.+Med. amt.+Core amt.)]

TABLE 1

Bovine Blood Wicking Results

| Experiment | Component | Initial Wt. | Final Wt. | Difference Amount | Percent |
|---|---|---|---|---|---|
| A | Cover | 0.265 | — | — | — |
|   | Medium A | 0.854 | — | — | — |
|   | Core | 10.907 | — | — | — |
| B | Cover | 0.247 | 0.365 | 0.118 | 4.4 |
|   | Medium B | 0.770 | 0.837 | 0.067 | 2.5 |
|   | Core | 11.145 | 13.618 | 2.473 | 93.0 |
| C | Cover | 0.336 | 0.358 | 0.022 | 0.7 |
|   | Medium C | 0.771 | 0.861 | 0.090 | 2.9 |
|   | Core | 11.052 | 13.992 | 2.940 | 96.3 |

For Experiment A, the cover was not placed over Medium A until after five minutes into the experiment. After the first five minutes, blood appeared in the center of Medium A, adjacent to the end of the needle, and at both ends of the medium. The cover then was placed over the medium and the experiment resumed. At the end of the 30-minute period, blood droplets were observed in the troughs of the medium. The medium was not wettable by blood and did not allow blood penetration.

In Experiment B, the cover had extensive spreading of blood and appeared to be wet by the blood equally on both sides. Medium B was wet on top with only one small spot of penetration into the troughs. The core had absorbed blood primarily in the areas not covered by the medium, having been absorbed from the edges of the cover.

Finally, the cover in Experiment C had a small spot of blood and was equally wet on both sides. The medium (Medium C) had blood in several troughs. The bottom of the medium appeared to be more wet than the top. Wicking was primarily in the Z direction; very little wicking in either the X or Y direction appeared to have taken place. The core had a stain pattern similar in size to that on the bottom of the medium and blood had penetrated through the entire thickness of the core.

From Experiments B and C, it is evident that treatment of the surfactant alone reduced the amount of blood retained by the cover to less than about 5 percent, whereas treatment of the medium with both surfactant and a corona field reduced the amount of blood retained by the cover to less than about 1 percent. In each case, the amount of blood retained by the medium remained below about 3 percent.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A Z-direction liquid transport medium defined by a plurality of generally V-shaped troughs, each of which has a bottom portion and a bifurcated top portion and is comprised of a fibrous web, in which:

the fibers are significantly oriented in a direction generally extending from the top portion of each trough to the bottom portion thereof;

the fibers are wettable by a liquid to which the Z-direction liquid transport medium may be exposed;

the density of the web at the bottom of each trough is greater than the density of the web in the remainder of the trough; and the fibers at the top portion of each trough are substantially discontinuous from the fibers at the top portions of adjacent troughs.

2. A Z-direction liquid transport medium of claim 1, in which the fibers at the bottom portion of each trough are substantially continuous.

3. The Z-direction liquid transport medium of claim 1, in which the fibers are hydrophilic.

4. The Z-direction liquid transport medium of claim 1, in which the surfaces of the fibers are hydrophilic.

5. The Z-direction liquid transport medium of claim 4, in which the fibers have been treated with a surfactant and exposed to a corona field.

6. The Z-direction liquid transport medium of claim 1, in which the fibrous web of which each generally V-shaped trough is comprised comprises a meltblown nonwoven web.

7. The Z-direction liquid transport medium of claim 1, in which the fibrous web of which each generally V-shaped trough is comprised comprises a neck-stretched, meltblown nonwoven web.

8. The Z-direction liquid transport medium of claim 1, in which the plurality of troughs are substantially parallel to each other.

9. The Z-direction liquid transport medium of claim 1, in which:

the fibers have been treated with a surfactant and exposed to a corona field;

the fibrous web of which each generally V-shaped trough is comprised comprises a neck-stretched, melt-blown nonwoven web; and the plurality of troughs are substantially parallel to each other.

10. A method of forming a Z-direction liquid transport medium comprising:

providing a fibrous web in which the fibers are significantly oriented in one direction and are wettable by a liquid to which the Z-direction liquid transport medium may be exposed;

forming the fibrous web into a plurality of troughs, each of which has a bottom portion and a bifurcated top portion, in a manner such that:

the fibers are significantly oriented in a direction generally extending from the top portion of each trough to the bottom portion thereof;

the density of the web at the bottom of each trough is greater than the density of the web in the remainder of the trough; and the fibers at the top portion of each trough are substantially discontinuous from the fibers at the top portions of adjacent troughs.

11. The method of claim 10, in which the fibrous web comprises a meltblown nonwoven web.

12. The method of claim 10, in which the fibrous web comprises a neck-stretched, meltblown nonwoven web.

13. The method of claim 10, in which the plurality of troughs are substantially parallel to each other.

* * * * *